United States Patent
McNeirney et al.

(10) Patent No.: US 6,679,267 B2
(45) Date of Patent: Jan. 20, 2004

(54) STERILE DRAPE FOR USE WITH LASER TRACKING SYSTEM

(75) Inventors: John C. McNeirney, Fairburn, GA (US); William H. Burns, Jr., Orchard Park, NY (US)

(73) Assignee: Minrad Inc., Buffalo, NY (US)

( * ) Notice: Subject to any disclaimer, the term of this patent is extended or adjusted under 35 U.S.C. 154(b) by 40 days.

(21) Appl. No.: 09/945,226

(22) Filed: Aug. 31, 2001

(65) Prior Publication Data

US 2002/0000231 A1 Jan. 3, 2002

Related U.S. Application Data

(62) Division of application No. 09/196,370, filed on Nov. 19, 1998, now Pat. No. 6,283,125.
(60) Provisional application No. 60/060,051, filed on Sep. 25, 1997.

(51) Int. Cl.[7] ............................................... A61B 19/08
(52) U.S. Cl. ....................................... 128/853; 359/510
(58) Field of Search ...................... 128/849, 852–854; 359/507, 510, 511–514, 818; 396/25, 27–29; 356/247; 378/205, 206; 385/129

(56) References Cited

U.S. PATENT DOCUMENTS

| | | | |
|---|---|---|---|
| 3,588,255 A | * | 6/1971 | Alexander .................. 356/247 |
| 3,721,234 A | | 3/1973 | Hadtke et al. |
| 4,308,864 A | | 1/1982 | Small et al. |
| 4,903,710 A | | 2/1990 | Jessamine et al. |
| 4,905,710 A | | 3/1990 | Jones |
| 4,998,538 A | | 3/1991 | Charowsky et al. |
| 5,048,942 A | * | 9/1991 | Ohbayashi .................. 359/513 |
| 5,307,368 A | * | 4/1994 | Hamar ........................ 356/247 |
| 5,433,221 A | | 7/1995 | Adair |
| 5,490,524 A | * | 2/1996 | Williams et al. ............. 128/849 |
| 5,497,268 A | * | 3/1996 | Tang ........................... 359/513 |
| 5,537,453 A | * | 7/1996 | Williams et al. ............ 378/206 |
| 5,591,119 A | | 1/1997 | Adair |
| 5,608,574 A | * | 3/1997 | Heinrich ..................... 359/510 |
| 5,665,073 A | | 9/1997 | Bulow et al. |
| 5,898,522 A | * | 4/1999 | Herpst ......................... 359/511 |
| 6,257,730 B1 | * | 7/2001 | Kleinberg et al. ........... 359/510 |
| 6,283,125 B1 | * | 9/2001 | McNeirney et al. ........ 128/853 |

* cited by examiner

Primary Examiner—Nicholas D. Lucchesi
Assistant Examiner—Victor Hwang
(74) Attorney, Agent, or Firm—Hodgson Russ LLP

(57) ABSTRACT

A sterile drape serving to preserve the sterile integrity of an operating field is disclosed. The drape has a rigid optically clear window which allows a visible light beam, such as a laser beam, to exit a targeting device without refraction or distortion that could result in misalignment of the visible light beam relative to a targeted object. The rigid optically clear window is made of a material having an ability to transmit light and which ability remains substantially unchanged after the drape has undergone a gamma radiation sterilization process. The drape is positioned so that the optically clear window is located across the device window. The optically clear window is adjusted with respect to the device window so that a secondary light beam caused by distortion due to misalignment of the windows disappears and only the visible light beam travels toward the targeted object.

1 Claim, 5 Drawing Sheets

STERILE DRAPE FOR USE WITH LASER TRACKING SYSTEM

CROSS REFERENCE TO A RELATED APPLICATION

This application is a division of application Ser. No. 09/196,370 now U.S. Pat. No. 6,283,125 issued Sep. 4, 2001 and. claims priority of earlier filed provisional patent application Ser. No. 60/060,051, filed on Sep. 25, 1997, which is incorporated herein by reference.

BACKGROUND OF THE INVENTION

1. Field of the Invention

The present invention relates generally to the field of undistorted transmission of a collimated visible light beam through an optically clear material. More particularly, the invention relates to a sterile drape, which allows a laser beam to pass through a clear portion of the drape while maintaining clarity of projection and precision of alignment of the beam. The drape helps maintain a sterile environment in an operating or diagnostic setting where a laser targeting system and imaging equipment, such as a fluoroscope, are used.

2. Background Art

Many diagnostic and surgical procedures involving complex devices or calling for use of multiple medical tools and pieces of equipment must be performed in a sterile operating environment. Most known medical procedures require a surgeon or a technician to identify a position of a particular region of interest inside a patient's body and later access that region to perform the required operation. Identifying a region of interest inside the patient is often done with the help of imaging equipment, such as fluoroscopes, computer tomographs (CT scanners), or magnetic resonance imaging equipment (MRI), which are commonly known and widely used for diagnostic and surgical purposes.

Imaging equipment is often used in conjunction with a targeting system, which emits a collimated visible light beam, such as a laser beam. In many applications the laser beam is used by a surgeon to specify the location and direction of entry into a patient's body for such procedures as biopsies, bone fixations and other precision operations normally performed using fluoroscopic methods.

When the desired region, or a subsurface target, inside a patient is ascertained, a surgeon needs to determine the preferred path of approaching and reaching the target in order to perform a surgery or another invasive medical procedure. A targeting system helps the surgeon to determine such a path. The visible light beam of the targeting system illuminates the selected path, making it a visible and convenient guide to the subsurface target. The direction of the light beam represents the angle of approach to the target. Furthermore, the light beam projects a dot on the skin of the patient, marking it as a point of entry to the internal region of interest, so that the region can be reached with a minimal error. An example of a laser targeting system for use during fluoroscopic procedures is a Dual Radiation Targeting System (DRTS), manufactured and marketed by MINRAD.

It is also often the case that the imaging equipment or the targeting system used with the imaging equipment can not be easily sterilized, so various sterile drapes are used to maintain sterile conditions in the room where operations or diagnostic procedures are performed. Standard sterile drapes are usually pliable plastic drapes. These drapes are usually clear and acceptable for many applications, including those requiring a user to operate equipment through the drape. However, such drapes can not provide clarity required for laser transmission. Without a drape, the accuracy of a laser beam is +/−1 mm at a distance of 1 meter, and the laser beam projects a dot approximately 1 mm in diameter. When propagating through clear drapes, the laser beam is usually distorted both in clarity of the projection of the dot and in the precision of identification of the subsurface target to which the surgeon is directed by the beam.

Sterile drapes known in the art and used specifically for imaging and targeting equipment are usually optically clear, or transparent, but these drapes distort the quality of projection of the laser beam in both clarity and direction for a variety of reasons. Furthermore, any movement or displacement of the drape from its intended position, can alter the clarity of transmission and precision of projection of the laser beam on the skin of the patient. Errors in the position of the beam or in the location of the entry point are consistently created by the use of existing sterile drapes.

For example, U.S. Pat. No. 5,490,524 to Williams et al. discloses a surgical drape for use with a laser targeting device mounted on an x-ray machine. In that patent a transparent window of flexible acetate film is attached to the x-ray transparent sheet material of the drape. There are two apparent disadvantages in the flexible acetate window disclosed in that patent. The first disadvantage relates to the fact that a flexible window may become curved from packaging or storage pressure, or when the drape is wrapped around laser targeting device. If the drape bends or curves, it becomes a cross section of a meniscus lens, diverting an incident light beam from its desired direction. The second disadvantage lies in the inability of is acetate films to withstand the process standardly used to sterilize surgical drapes during manufacture—the gamma radiation sterilization. This type of sterilization causes acetate to yellow, thus, affecting the transmission of light having frequencies above 600 nm. It would be desirable, of course, to have a drape with an optically clear window made of such a material on which optical properties gamma sterilization will have minimal or no effect.

It would be also desirable to provide a drape which could be maintained in correct alignment with a targeting device in order to allow the light beam to exit the targeting device without refraction or distortion.

SUMMARY OF THE INVENTION

Accordingly it is an object of the present invention to provide for an optical window through which a laser beam can be transmitted without distortion or displacement.

It is another object of the present invention to provide an optically clear window which resists bending and remains rigid during packaging, storage and use.

It is yet another object of the present invention to provide a sterile surgical drape with an optically clear rigid window made of a material with optical properties remaining unaffected by the gamma-radiation sterilization process.

It is also an object of the present invention to provide a surgical drape with a window, which will allow one to detect misalignment between the disk and a laser beam of the laser targeting device.

The sterile drape of the present invention overcomes disadvantages described with regard to existing sterile drapes. The present invention provides a sterile drape, which consists of two components: a sterile bag for covering a targeting device and a window for clear and undistorted transmission of the light beam emitted by the targeting device.

The sterile drape includes a plastic drape with an optically clear window made of a variety of optically clear polymers that resist bending or curving. The drape is adapted to being wrapped around a targeting device used together with imaging equipment, such as, for example, a fluoroscope. Both clarity and precision of projection of the laser beam are preserved when the window is properly aligned on the laser targeting device. If the window is misaligned, the laser beam projects a primary beam and a second, smaller laser beam, which is refracted away by the misaligned window from the desired path and location. The second beam, therefore, serves as an indicator of the degree and direction of misalignment. When the misalignment is detected, the positions of the window and the drape can be easily adjusted on the targeting device with the help of a drape window positioning device to allow for the undistorted and undeflected transmission of the laser beam from the targeting device to the patient.

Still other objects and advantages of the present invention will become readily apparent to those skilled in this art from the following detailed description, wherein a preferred embodiment is shown and described, simply by way of illustration of the best mode contemplated by the inventor for carrying out the invention. As will be realized, the invention is capable of other and different embodiments and its several details are capable of modifications in various obvious respects, all without departing from the invention. Accordingly, the drawings and description are to be regarded as illustrative in nature and not as restrictive.

BRIEF DESCRIPTION OF THE DRAWINGS

For a further understanding of the invention, as well as its characterizing features, reference should now be made to the accompanying drawings wherein.

DETAILED DESCRIPTION OF THE PREFERRED EMBODIMENT

Figure 1:
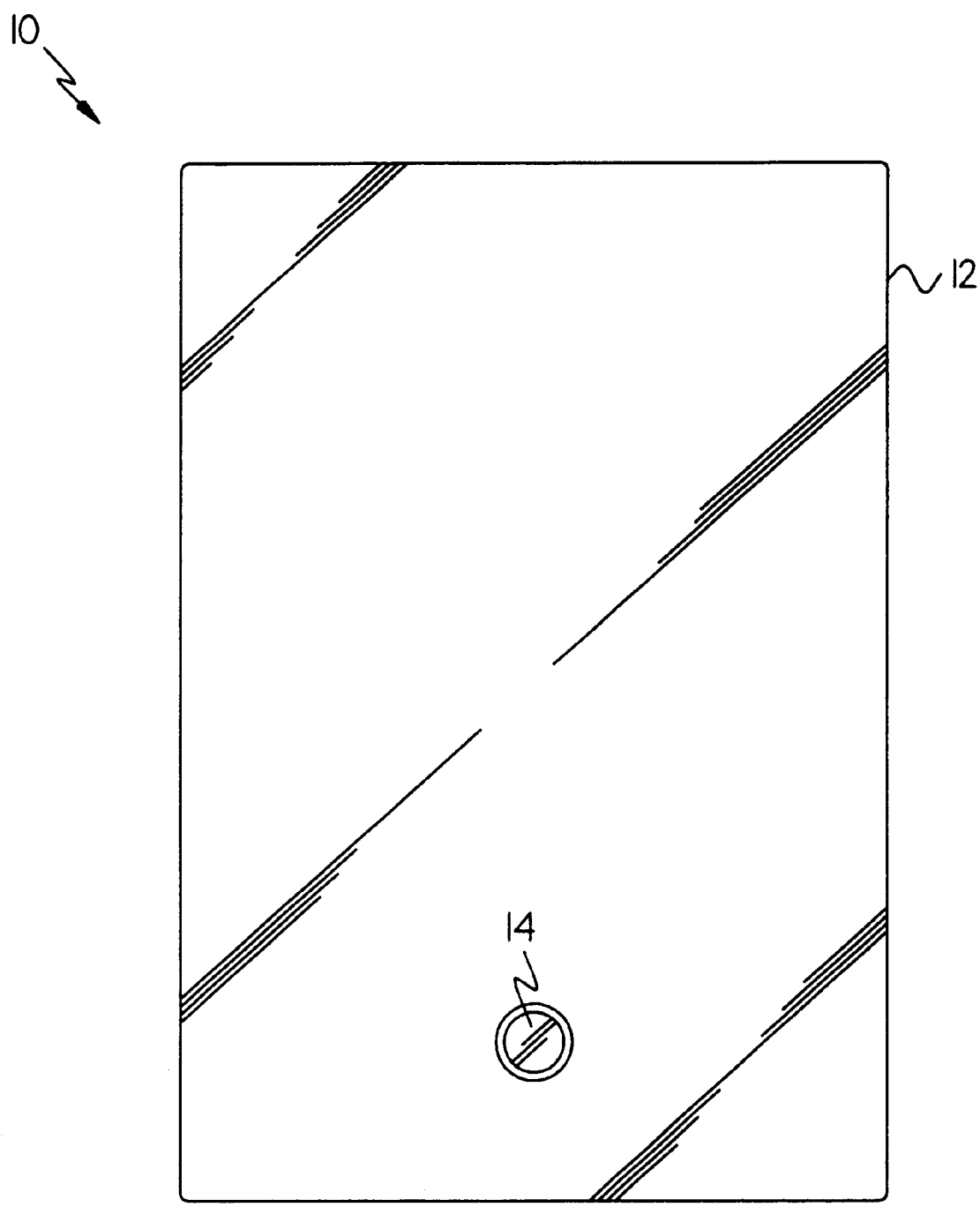
FIG. 1 is a schematic diagram showing the dimensions of the drape including an optically clear window through which a laser beam may be transmitted.

In accordance with the present invention, shown in FIG. 1 is a drape 10 having a sterile bag 12 and a window 14. Drape 10 is adapted for use with various targeting devices used in imaging procedures, such as a targeting system 20 shown in FIGS. 2 and 3. In the preferred embodiment of the present invention drape 10 is used with a Dual Radiation Targeting System (DRTS), described in U.S. Pat. Nos. 5,212,720 and 5,644,616, manufactured by MINRAD Inc., which Patents are incorporated herein by reference. The DRTS is a laser targeting system for use with fluoroscopic procedures which projects a red, Class IIIa laser beam onto a patient.

Figure 4:
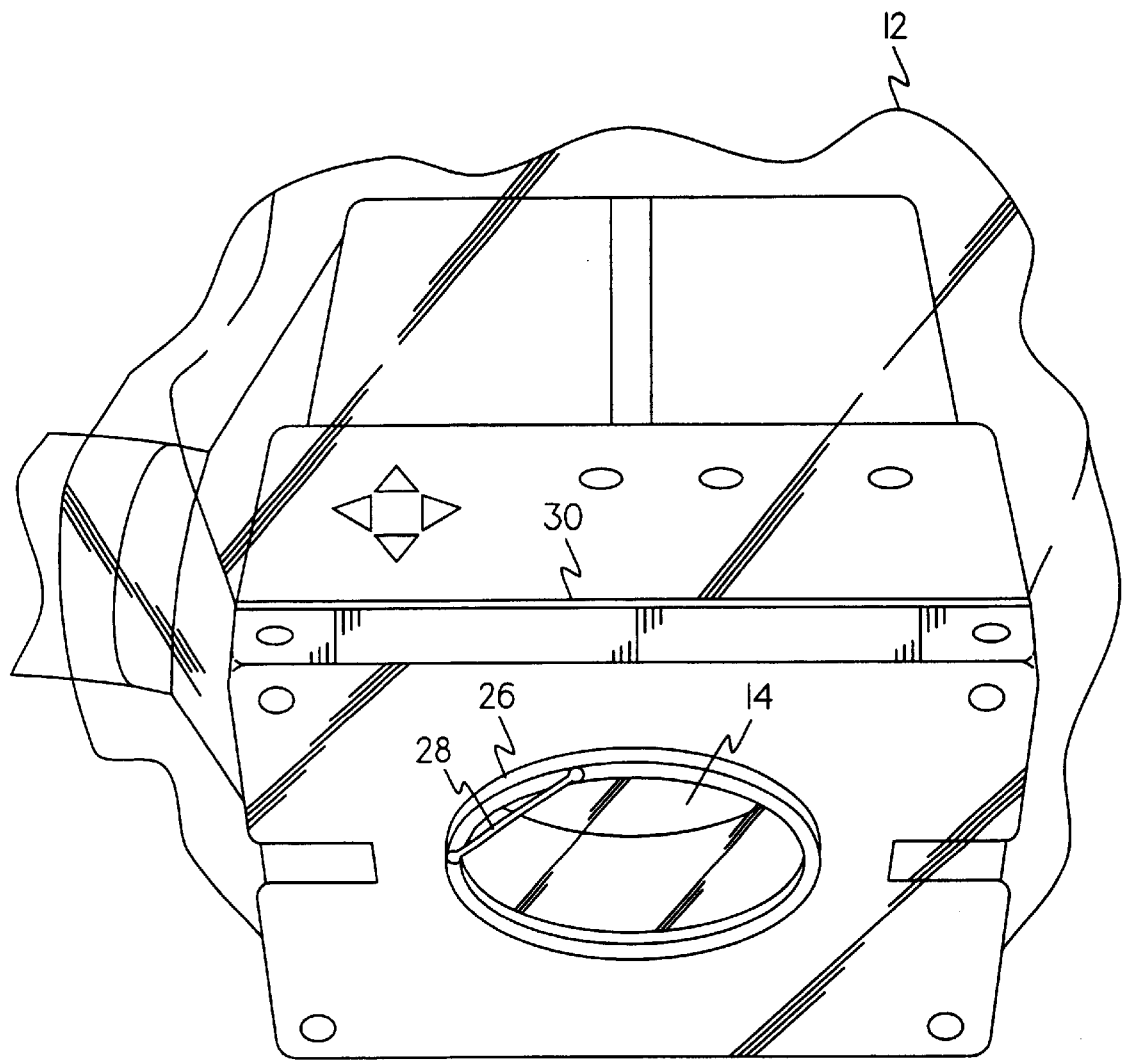
FIG. 4 is a perspective view of a laser targeting device with the sterile drape of the present invention.

Sterile bag 12 can be made of any plastic material conventionally used to manufacture surgical drapes. Preferably, sterile bag 12 is made of 0.0015 inch low density polyethylene. The size of the bag is such that it can wrap around targeting device 20 to protect the equipment and the patient from contamination, as illustrated in FIG. 4.

Figure 2:
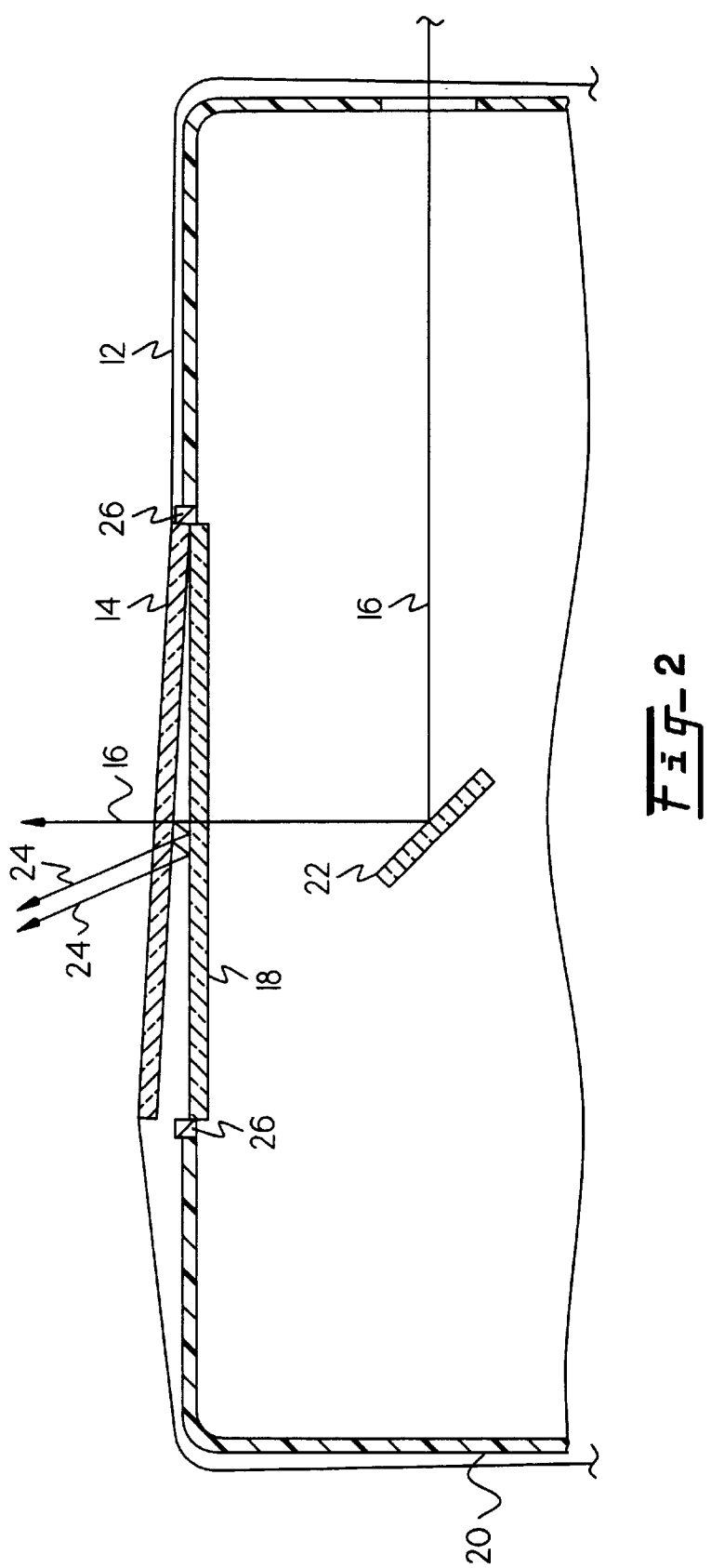
FIG. 2 is a schematic representation of misalignment between the window of the drape of the present invention and a laser targeting device.
Figure 3:
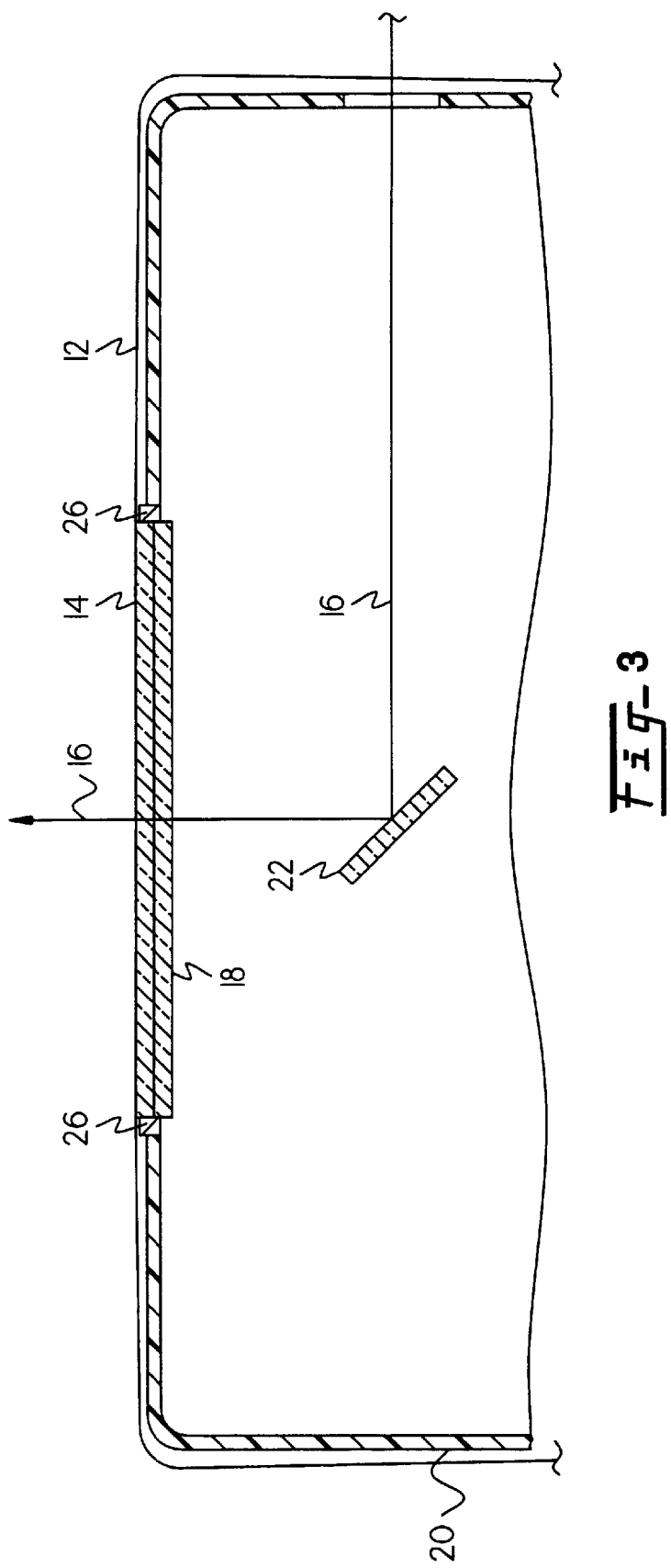
FIG. 3 is a schematic representation of the window of the drape of the present invention secured in the aligned position by the drape window positioning ridge.

In order to maintain the clarity and precision of projection and position of a light beam, sterile drape 10 also includes a hard, rigid, clear plastic window 14 through which a visible light beam, such as a light beam 16 shown in FIGS. 2 and 3, can be transmitted. Preferably, window 14 has a disk-like shape. Window 14 can be attached to sterile bag 12 by any method which will bond the surface of window 14 and sterile bag 12 together such as, for example, ultrasonic welding, heat sealing, solvent welding or gluing. Window 14 is made of an optically clear material, such as, for example, polyethylene terephalate glycol (PETG), but a variety of optically clear polymers, such as polycarbonate or acrylic polymers, can be used as a suitable material. It is important for the purposes of the present invention that the polymer of window 14 is rigid, because a thin film or a flexible polymer will inevitably bend or curve either before or during the use of drape 10 on targeting device 20. A curved window will serve as a lens defocusing and deflecting light beam 16 from its desired direction. PETG used in the preferred embodiment of the sterile drape of the present invention is rigid enough to resist bending or curving, thus, maintaining window 14 in the non-bent shape, which is best suited for transmission of light beam 16. The disk window of the sterile drape is made thick enough to be hard, rigid and non-flexible. This property of the window provides for resistance to bending or curving during manufacture, storage, transportation or use. Another advantage of using the PETG polymer for window 14 is in its suitability for sterilization by gamma radiation, a standard procedure used to sterilize surgical drapes during manufacture. PETG is resistant to tinting or acquiring shades of color during irradiation by gamma rays, therefore, ensuring clear transmission of laser beams of various wave lengths through window 14 during targeting procedures.

When in use, sterile drape 10 is wrapped around targeting device 20, so that window 14 of the drape is positioned "face-to-face" with a targeting device window 18, as illustrated in FIG. 3. In the preferred embodiment of the invention, targeting device window 18 is made of PETG. As shown in FIG. 4, a securing means 30 helps sterile drape 10 to fit over targeting device 20 and remain wrapped around the targeting device during a medical procedure. In the preferred embodiment of the present invention securing means 30 is a rubber band.

In the preferred embodiment, light beam 16 is a laser beam generated in targeting device 20 and directed through targeting device window 18 by a mirror 22. As can be seen in FIG. 3, in order for light beam 16 to propagate in the desired direction, the present invention calls for as minimal distortion, deflection or refraction of light beam 16 on its way from targeting device 20 to the patient as possible. If window 14 is misaligned with respect to targeting device window 18, as shown in FIG. 2, then a part of light beam 16 is going to be refracted away from the desired direction of light beam 16, thus, deteriorating clarity and precision of projection of the beam. The refracted part of light beam 16 is shown as a one or more secondary beam 24 in FIG. 2. In such a case the presence of secondary beam 24 causes targeting device 20 to project not a dot, but a blurred spot on the skin of a patient, decreasing the precision of indication of where the point of entry to the subsurface target inside the patient is. Additionally, the presence of secondary beam 24 blurs the line along which light beam 16 is supposed to propagate, thus deteriorating the precision of illumination of the direction of approach to the subsurface target.

Figure 5:
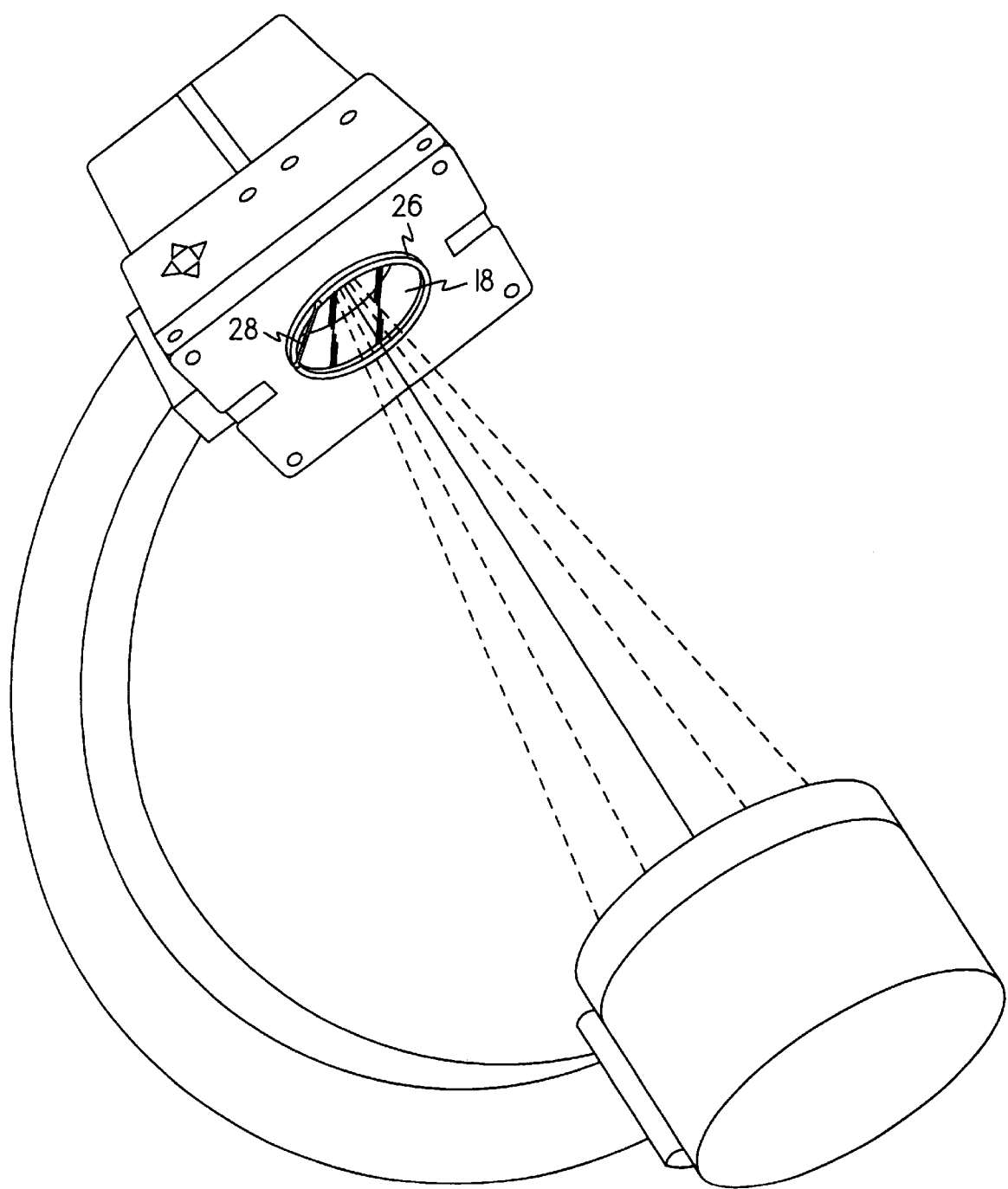
FIG. 5 is a perspective view of a laser targeting device with the holding element of the present invention.

In order to ensure and maintain the correct alignment of window 14 of the sterile drape and targeting device window 18 during an operation or a diagnostic procedure, the present invention provides for a window holding element 28, illustrated in FIG. 5. In the preferred embodiment of the present invention holding element 28 is a spring or a pin, but any elongated structure suitable for holding window 14 can be employed. Both ends of holding element 28 are attached to a window positioning ridge 26, illustrated in FIGS. 2, 3, and 5. When sterile drape 10 is used with laser targeting device 20, a part of window 14 is slipped under holding element 28 to ensure that window 14 stays properly aligned on targeting device 20. Securing means 30 is also used to keep the drape wrapped around targeting device 20.

It is intended that the above description of preferred embodiments of the structure of the present invention and the description of its operation are but one or two enabling best mode embodiments for implementing the invention. Other modifications and variations are likely to be conceived of by those skilled in the art upon a reading of the preferred embodiments and a consideration of the appended claims and drawings. These modifications and variations still fall within the breadth and scope of the disclosure of the present invention.

What is claimed is:

1. A method of undistorted transmission of a visible light beam through an optically clear window along a predetermined direction, the visible light beam being generated by a targeting device having a device window disposed in a plane and a holding element, the method comprising:

providing a protective cover having a flexible body and an optically clear window therein;

placing the protective cover on the targeting device to position the optically clear window across the device window between the device window and the holding element;

determining the presence of a secondary light beam produced as a result of distortion of the visible light beam propagating through the optically clear window when the optically clear window is misaligned with the plane of the device window; and adjusting the optically clear window with respect to the device window when the presence of the secondary light beam has been determined, so that the secondary light beam disappears and only the visible light beam travels along the predetermined direction.

* * * * *